(12) United States Patent
Yoshino

(10) Patent No.: US 10,129,454 B2
(45) Date of Patent: Nov. 13, 2018

(54) IMAGING DEVICE, ENDOSCOPE APPARATUS, AND METHOD FOR CONTROLLING IMAGING DEVICE

(71) Applicant: OLYMPUS CORPORATION, Shibuya-ku, Tokyo (JP)

(72) Inventor: Koichiro Yoshino, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 939 days.

(21) Appl. No.: 14/229,168

(22) Filed: Mar. 28, 2014

(65) Prior Publication Data

US 2014/0210974 A1 Jul. 31, 2014

Related U.S. Application Data

(63) Continuation of application No. PCT/JP2012/076172, filed on Oct. 10, 2012.

(30) Foreign Application Priority Data

Oct. 21, 2011 (JP) .................................. 2011-231947

(51) Int. Cl.
    *H04N 5/232* (2006.01)
    *G02B 23/24* (2006.01)
    (Continued)

(52) U.S. Cl.
    CPC ..... *H04N 5/23212* (2013.01); *A61B 1/00188* (2013.01); *A61B 1/05* (2013.01);
    (Continued)

(58) Field of Classification Search
    CPC .... G02B 23/243; G02B 7/09; H04N 5/23212; H04N 5/23296; G03B 13/36; A61B 1/00188; A61B 1/05; A61B 1/00096
    See application file for complete search history.

(56) References Cited

U.S. PATENT DOCUMENTS

| 4,312,572 A | 1/1982 | Yamashita et al. |
| 6,829,008 B1 | 12/2004 | Kondo et al. |

(Continued)

FOREIGN PATENT DOCUMENTS

| CN | 101184163 A | 5/2008 |
| JP | 10-239579 A | 9/1998 |

(Continued)

OTHER PUBLICATIONS

International Search Report (ISR) dated Jan. 15, 2013 (and English translation thereof) issued in International Application No. PCT/JP2012/076172.

(Continued)

*Primary Examiner* — Obafemi O Sosanya
(74) *Attorney, Agent, or Firm* — Holtz, Holtz & Volek PC

(57) ABSTRACT

The imaging device includes an imaging optical system that includes a movable lens that simultaneously adjusts the angle of view and the in-focus object distance, an image sensor, a plurality of phase sensors, an acquisition section (A/D conversion section) that acquires phase information from the plurality of phase sensors, a lens control section that controls the position of the movable lens, and a moving amount calculation section that calculates the moving amount of the movable lens necessary for implementing an in-focus state of an image formed on the image sensor due to light beams that have passed through the imaging optical system, based on a phase difference that is based on the phase information, the lens control section controlling the position of the movable lens based on the moving amount calculated by the moving amount calculation section.

13 Claims, 10 Drawing Sheets

(51) Int. Cl.
  *A61B 1/00* (2006.01)
  *H04N 5/369* (2011.01)
  *A61B 1/05* (2006.01)
  *G02B 7/34* (2006.01)
  *H04N 5/225* (2006.01)

(52) U.S. Cl.
  CPC ....... *G02B 23/2438* (2013.01); *H04N 5/3696* (2013.01); *G02B 7/34* (2013.01); *H04N 2005/2255* (2013.01)

(56) References Cited

U.S. PATENT DOCUMENTS

| | | | |
|---|---|---|---|
| 2002/0003955 A1 | 1/2002 | Yamaguchi | |
| 2003/0081137 A1* | 5/2003 | Yamazaki | H04N 5/23212 348/354 |
| 2005/0174474 A1* | 8/2005 | Hasegawa | H04N 5/2352 348/370 |
| 2008/0118238 A1 | 5/2008 | Sogawa et al. | |
| 2008/0291311 A1 | 11/2008 | Kusaka | |
| 2009/0115882 A1* | 5/2009 | Kawarada | G03B 7/28 348/340 |
| 2009/0167924 A1* | 7/2009 | Raschke | G03B 13/32 348/345 |
| 2010/0091175 A1* | 4/2010 | Shintani | G02B 7/365 348/345 |
| 2010/0194967 A1* | 8/2010 | Amano | G02B 7/34 348/345 |
| 2011/0157721 A1* | 6/2011 | Ohtake | G02B 7/102 359/695 |
| 2012/0033120 A1 | 2/2012 | Nakamura et al. | |
| 2015/0181108 A1* | 6/2015 | Endo | G02B 7/34 348/345 |

FOREIGN PATENT DOCUMENTS

| | | |
|---|---|---|
| JP | 2000-156823 A | 6/2000 |
| JP | 2001324662 A | 11/2001 |
| JP | 2002253488 A | 9/2002 |
| JP | 2002258164 A | 9/2002 |
| JP | 2002369795 A | 12/2002 |
| JP | 2004-294788 A | 10/2004 |
| JP | 2006-091252 A | 4/2006 |
| JP | 2009-037262 A | 2/2009 |
| JP | 2010176092 A | 8/2010 |
| JP | 2010252277 A | 11/2010 |
| JP | 2011-075841 A | 4/2011 |
| WO | 2009020031 A1 | 2/2009 |
| WO | 2010004728 A1 | 1/2010 |
| WO | 2010055797 A1 | 5/2010 |
| WO | 2010122702 A1 | 10/2010 |

OTHER PUBLICATIONS

Japanese Office Action (and English translation thereof) dated Sep. 29, 2015, issued in counterpart Japanese Application No. 2011-231947.
Extended European Search Report dated Jun. 24, 2015, issued in counterpart European Application No. 12842285.4.
Chinese Office Action (and English translation thereof) dated Nov. 26, 2015, issued in Chinese Application No. 201280051353.3.
European Office Action dated Oct. 18, 2017 issued in counterpart European Application No. 12842285.4.

* cited by examiner

FIG. 12

| POSITION OF MOVABLE LENS | RATIO OF MOVING AMOUNT OF MOVABLE LENS TO MOVING AMOUNT OF IMAGE POSITION |
|---|---|
| x1 | R1 |
| x2 | R2 |
| x3 | R3 |
| ⋮ | ⋮ |

FIG. 13

| POSITION OF MOVABLE LENS | RATIO OF MOVING AMOUNT OF MOVABLE LENS TO MOVING AMOUNT OF IMAGE POSITION | DISTANCE BETWEEN IMAGE PLANE AND EXIT PUPIL | DISTANCE BETWEEN CENTERS OF GRAVITY OF PUPILS |
|---|---|---|---|
| x1 | R1 | F1 | G1 |
| x2 | R2 | F2 | G2 |
| x3 | R3 | F3 | G3 |
| ⋮ | ⋮ | ⋮ | ⋮ |

IMAGING DEVICE, ENDOSCOPE APPARATUS, AND METHOD FOR CONTROLLING IMAGING DEVICE

CROSS REFERENCE TO RELATED APPLICATION

This application is a continuation of International Patent Application No. PCT/JP2012/076172, having an international filing date of Oct. 10, 2012, which designated the United States, the entirety of which is incorporated herein by reference. Japanese Patent Application No. 2011-231947 filed on Oct. 21, 2011 is also incorporated herein by reference in its entirety.

BACKGROUND

The present invention relates to an imaging device, an endoscope apparatus, a method for controlling an imaging device, and the like.

An endoscope system having a zoom function has been put to practical use, the endoscope system being configured so that the entire digestive tract (object) is observed on the wide-angle (WIDE) side (normal observation), and part of the digestive tract is observed in a zoom state on the telescopic (TELE) side (zoom observation) by adjusting the angle of view of the objective lens by moving a movable lens.

The endoscope system having a zoom function is normally configured to implement the magnification necessary for zoom observation by moving the movable lens to reduce the angle of view on the TELE side (i.e., increase the optical magnification) while adjusting the focal distance to reduce the best object distance. The term "best object distance" used herein refers to the distance from the end of the objective lens to the object when the image position of the object coincides with the image plane of the image sensor. Since the object can be more closely observed by reducing the best object distance on the TELE side, the magnification during zoom observation can be increased.

On the other hand, since the moving amount of the image position due to the movement of the position of the object increases as the best object distance decreases, the depth of field of the optical system normally becomes shallow. Since the TELE-side depth of field of an endoscope system having a zoom function developed in recent years may be 1 mm or less, it may be difficult for the user to bring the object into focus.

In order to solve the above problem, JP-A-2004-294788 proposes an endoscope system having an autofocus (AF) function (contrast AF function) that calculates a contrast value (i.e., an evaluation value that indicates the degree of in-focus of the image) from a high-frequency component of the image to evaluate the in-focus state, for example. JP-A-10-239579 proposes a video camera having a function (continuous AF function) that calculates a contrast value while wobbling the focus lens to detect the in-focus direction, and cyclically controlling the focus lens so that the focal distance moves in the in-focus direction to continuously bring the object into focus so as to follow the object in a movie.

It is difficult to maintain the distance (object distance) from the end of the objective lens to the object to be constant during zoom observation using an endoscope due to pulsation of the object and the like. Therefore, even if the user has temporarily brought the object into focus using a single AF operation, the object becomes out of focus due to a change in the object distance, and observation by the user is hindered. It is desirable to perform the continuous AF operation (see JP-A-10-239579) in order to solve the above problem. However, when detecting the in-focus direction from the contrast value as disclosed in JP-A-10-239579, it is necessary to minimize a change in angle of view due to the movement of the focus lens in order to acquire a natural image that does not flicker during wobbling. Therefore, when using an optical system that simultaneously adjusts the angle of view and the best object distance by moving the movable lens such as that used for the endoscope system having a zoom function, it is difficult to wobble the movable lens as the focus lens.

The zoom function and the continuous AF operation may be simultaneously implemented by employing an optical system that includes a zoom lens that mainly adjusts the optical magnification, and a focus lens that mainly adjusts the focal distance (e.g., in-focus object plane position (i.e., the position of the object in an in-focus state)) of the optical system, and independently controlling the zoom lens and the focus lens, for example.

SUMMARY

According to one aspect of the invention, there is provided an imaging device comprising:

an imaging optical system that includes a movable lens that is configured so that an in-focus object distance is changed along with a change in angle of view;

an image sensor; a plurality of phase sensors;

an acquisition section that acquires phase information from the plurality of phase sensors;

a lens control section that controls a position of the movable lens; and a moving amount calculation section that calculates a moving amount of the movable lens necessary for implementing an in-focus state of an image formed on the image sensor due to light beams that have passed through the imaging optical system, based on a phase difference that is based on the phase information acquired by the acquisition section, the lens control section controlling the position of the movable lens based on the moving amount calculated by the moving amount calculation section.

According to another aspect of the invention, there is provided an endoscope apparatus comprising:

an imaging optical system that includes a movable lens that is configured so that an in-focus object distance is changed along with a change in angle of view;

an image sensor;

a plurality of phase sensors;

an acquisition section that acquires phase information from the plurality of phase sensors;

a lens control section that controls a position of the movable lens; and a moving amount calculation section that calculates a moving amount of the movable lens necessary for implementing an in-focus state of an image formed on the image sensor due to light beams that have passed through the imaging optical system, based on a phase difference that is based on the phase information acquired by the acquisition section, the lens control section controlling the position of the movable lens based on the moving amount calculated by the moving amount calculation section.

According to another aspect of the invention, there is provided a method for controlling an imaging device comprising:

acquiring phase information from a plurality of phase sensors;

calculating a moving amount of a movable lens necessary for implementing an in-focus state of an image formed on an image sensor due to light beams that have passed through an imaging optical system, based on a phase difference based on the acquired phase information; and controlling a position of the movable lens based on the calculated moving amount, the movable lens being a lens that is included in the imaging optical system and configured so that an in-focus object distance is changed along with a change in angle of view.

BRIEF DESCRIPTION OF DRAWINGS

FIG. 12 is a view illustrating an example of a data structure that links the position of a movable lens and a parameter.

FIG. 13 is a view illustrating another example of a data structure that links the position of a movable lens and a parameter.

DESCRIPTION OF EXEMPLARY EMBODIMENTS

Figure 1:
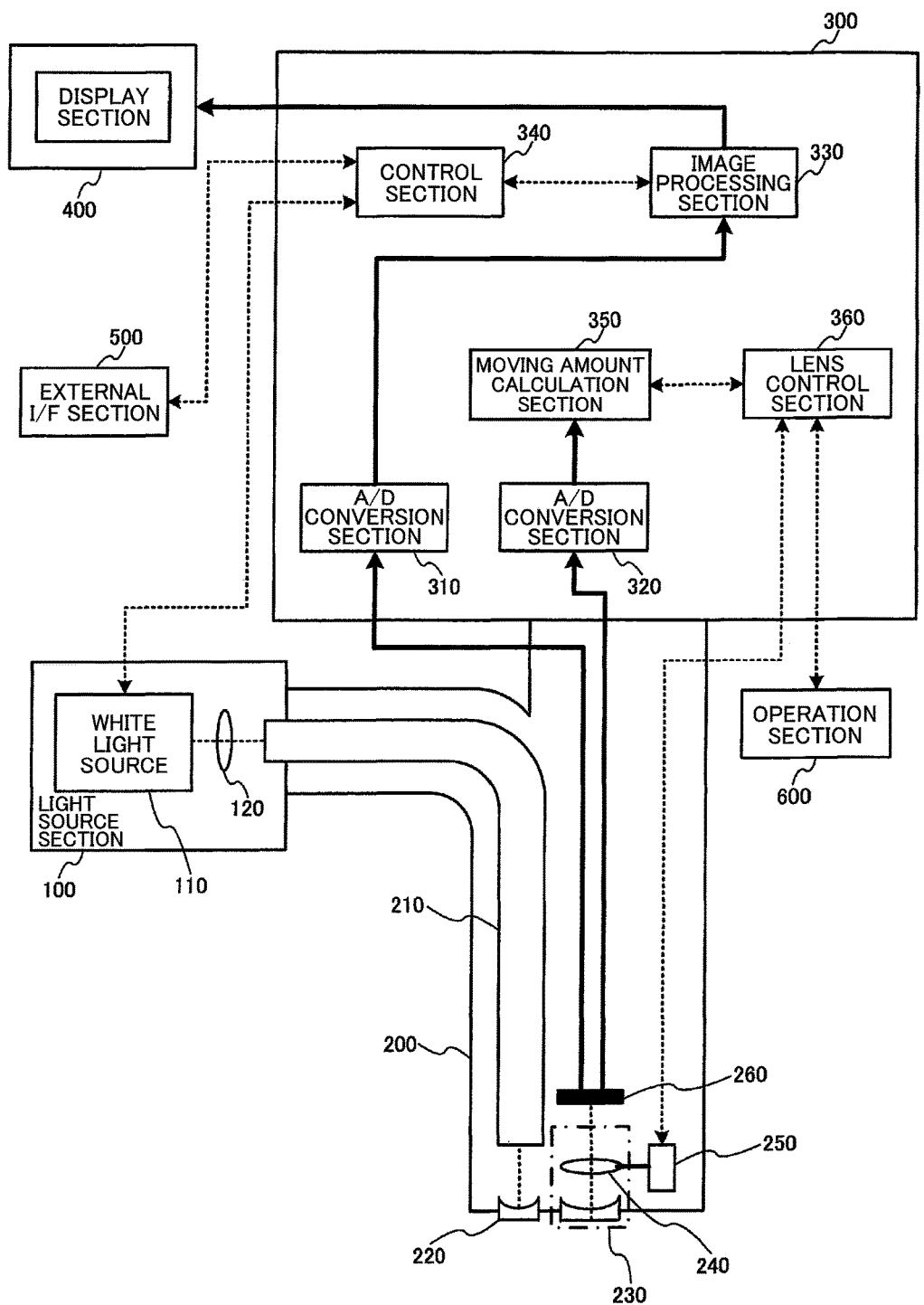
FIG. 1 illustrates a configuration example of an imaging device according to a first embodiment and an endoscope apparatus including the same.

According to one embodiment of the invention, there is provided an imaging device comprising:

an imaging optical system that includes a movable lens that simultaneously adjusts an angle of view and an in-focus object distance;

an image sensor; a plurality of phase sensors;

an acquisition section that acquires phase information from the plurality of phase sensors;

a lens control section that controls a position of the movable lens; and a moving amount calculation section that calculates a moving amount of the movable lens necessary for implementing an in-focus state of an image formed on the image sensor due to light beams that have passed through the imaging optical system, based on a phase difference that is based on the phase information acquired by the acquisition section, the lens control section controlling the position of the movable lens based on the moving amount calculated by the moving amount calculation section.

According to one embodiment of the invention, the imaging optical system designed so that the angle of view and the in-focus object distance are changed by moving the movable lens is used. The moving amount of the movable lens is calculated based on the phase information from the phase sensors, and the position of the movable lens is controlled based on the calculated moving amount. Since the imaging optical system having a simple configuration is used, the size of the imaging device can be reduced while preventing a situation in which the image flickers that may occur during the focus operation that utilizes the imaging optical system when information other than the phase information is used.

According to another embodiment of the invention, there is provided an endoscope apparatus comprising:

an imaging optical system that includes a movable lens that simultaneously adjusts an angle of view and an in-focus object distance;

an image sensor;

a plurality of phase sensors;

an acquisition section that acquires phase information from the plurality of phase sensors;

a lens control section that controls a position of the movable lens; and a moving amount calculation section that calculates a moving amount of the movable lens necessary for implementing an in-focus state of an image formed on the image sensor due to light beams that have passed through the imaging optical system, based on a phase difference that is based on the phase information acquired by the acquisition section, the lens control section controlling the position of the movable lens based on the moving amount calculated by the moving amount calculation section.

According to another embodiment of the invention, there is provided a method for controlling an imaging device comprising:

acquiring phase information from a plurality of phase sensors;

calculating a moving amount of a movable lens necessary for implementing an in-focus state of an image formed on an image sensor due to light beams that have passed through an imaging optical system, based on a phase difference based on the acquired phase information; and controlling a position of the movable lens based on the calculated moving amount, the movable lens being a lens that is included in the imaging optical system and simultaneously adjusts an angle of view and an in-focus object distance.

Several exemplary embodiments of the invention are described below. Note that the following exemplary embodiments do not in any way limit the scope of the invention laid out in the claims. Note also that all of the elements described below in connection with the following exemplary embodiments should not necessarily be taken as essential elements of the invention.

1. Method

A method employed in connection with several embodiments of the invention is described below. When using an endoscope system that implements zoom observation, the depth of field may become very shallow when the imaging magnification is high, and the object distance is short. When the depth of field may become very shallow, it is difficult for the user (e.g., doctor) to manually bring the object into focus. This problem may be solved by performing the autofocus (AF) operation.

An imaging optical system may have a single-group-drive lens configuration or a dual-group-drive lens configuration. The term "single-group-drive lens configuration" used herein refers to a lens configuration in which the magnification (angle of view) and the focus (best object distance) are simultaneously adjusted by driving a single lens group. The term "dual-group-drive lens configuration" used herein refers to a lens configuration in which a lens group that adjusts the magnification (zoom lens group) and a lens group that adjusts the focus (focus lens group) are provided, and the magnification and the focus are adjusted independently. The dual-group-drive lens configuration has an advantage in that the degree of freedom of control can be improved. On the other hand, the single-group-drive lens configuration has an advantage in that a reduction in size and cost can be achieved due to a simple configuration. Therefore, the single-group-drive lens configuration may be used for an endoscope system, and the following exemplary embodiments are given on the assumption that the single-group-drive lens configuration is used.

However, a problem may occur when an AF operation (single AF operation or continuous AF operation (basically the single AF operation)) is performed using the single-group-drive lens configuration. When using the contrast AF technique, it is necessary to change the best object distance little by little through wobbling or the like. Since the magnification changes along with a change in the best object distance when using the single-group-drive lens configuration, the captured image flickers during the AF operation, and adversely affects observation by the user.

In order to solve the above problems, several aspects and embodiments of the invention propose a method that causes an imaging device having the single-group-drive lens configuration and suitable for an endoscope system to perform the AF operation using phase information from a phase sensor. Since the AF operation (phase detection AF) that utilizes the phase information does not require wobbling required for the contrast AF operation or the like, a situation in which the image flickers does not occur.

A first embodiment illustrates a basic system configuration example, a parameter acquisition process (e.g., values F, G, and R), an AF operation rate setting process, and the like. Although the method according several embodiments of the invention is based on the phase detection AF operation, the contrast AF operation may also be used when the phase detection AF operation is not effective. In such a case, whether or not the phase detection AF operation is effective is determined using a defocus index. A second embodiment illustrates a method that calculates the defocus index from the phase information, and a third embodiment illustrates a method that utilizes a contrast value as the defocus index.

2. First Embodiment

An imaging device according to the first embodiment and an endoscope system including the same are described below with reference to FIG. 1. The endoscope system according to the first embodiment includes a light source section 100, an imaging section 200, a processing section 300, a display section 400, an external I/F section 500, and an operation section 600.

The light source section 100 includes a white light source 110 that emits white light, and a condenser lens 120 that focuses the white light on a light guide fiber 210.

The imaging section 200 is formed to be elongated and flexible so that the imaging section 200 can be inserted into a body cavity or the like. The imaging section 200 includes the light guide fiber 210 that guides the light focused by the light source section 100, an illumination lens 220 that diffuses the light guided by the light guide fiber 210, and applies the diffused light to an observation target, an objective lens system 230 that forms an image of the reflected light from the observation target, a movable lens 240 that is included in the objective lens 230, and simultaneously adjusts the angle of view and the best object distance, a lens driver section 250 that drives the movable lens 240, and an image sensor 260 that photoelectrically converts the reflected light to generate an image.

Figure 9:
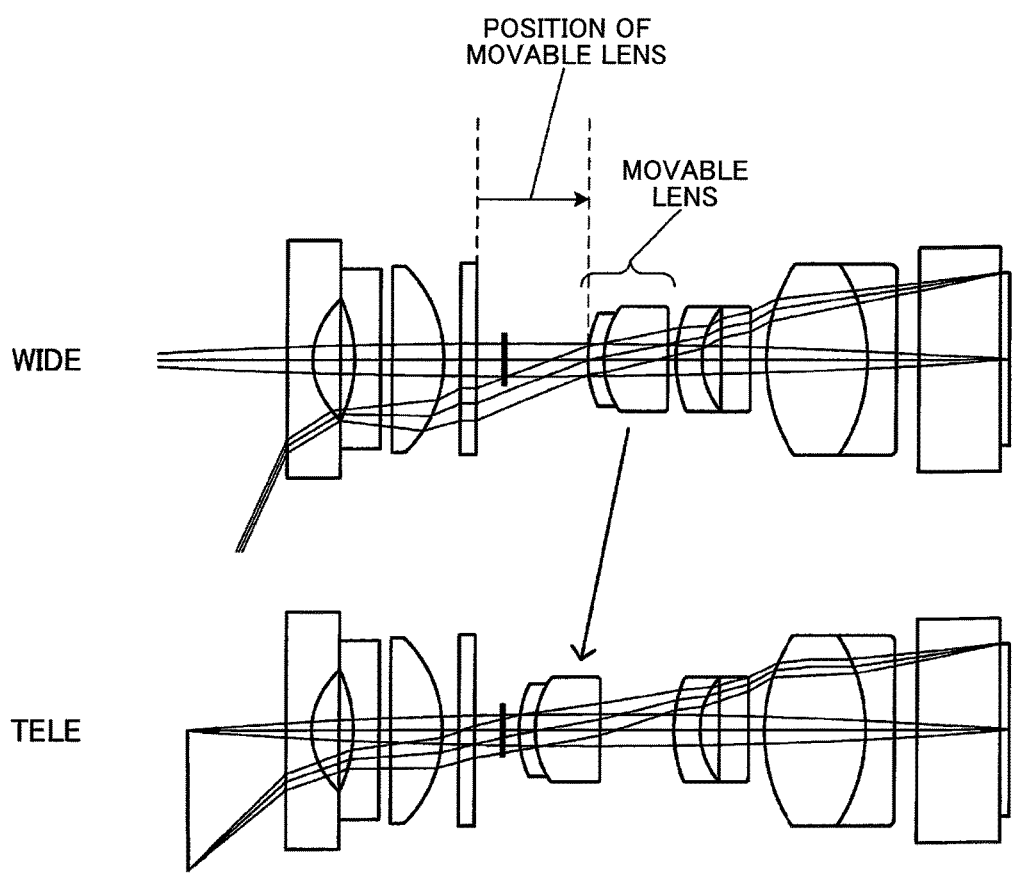
FIG. 9 illustrates a configuration example of an imaging optical system.

FIG. 9 illustrates an example of the objective lens 230 according to the first embodiment. The objective lens 230 is designed so that the angle of view becomes narrow (i.e., the optical magnification increases) and the best object distance (in-focus object distance in a broad sense) decreases when the position of the movable lens 240 is moved from the WIDE end to the TELE end in the same manner as in a known endoscope system having a zoom function.

The lens driver section 250 according to the first embodiment is implemented by a voice coil motor (VCM), for example. The image sensor 260 is an image sensor that includes a Bayer array (see FIG. 10), for example. The image sensor 260 is configured to include phase sensors S1 and S2. The details of the phase sensors S1 and S2 are described later.

The processing section 300 includes an A/D conversion sections 310 and 320, an image processing section 330, a control section 340, a moving amount calculation section 350, and a lens control section 360. The A/D conversion section 310 converts analog image signals output from the image sensor 260 into digital image signals, and outputs the digital image signals to the image processing section 330. The image processing section 330 performs image processing (e.g., white balance process, interpolation process (demosaicing process), color conversion process, grayscale transformation process, and noise reduction process) on the image signals output from the A/D conversion section 310, and outputs the resulting image signals to the display section 400. The display section 400 is a liquid crystal monitor, for example. The display section 400 displays the image signals output from the image processing section 330.

The A/D conversion section 320 converts analog phase signals output from the phase sensors S1 and S2 included in the image sensor 260 into digital phase signals, and outputs the digital phase signals to the moving amount calculation section 350. The moving amount calculation section 350 calculates the moving amount of the movable lens 240 from the phase signals output from the A/D conversion section 320, and outputs the calculated moving amount to the lens control section 360. The details of the moving amount calculation section 350 are described later.

The lens control section 360 is connected to the operation section 600 and the lens driver section 250, and controls the position of the movable lens 240 based on the moving amount output from the moving amount calculation section 350 according to control information output from the operation section 600. The position x of the movable lens 240 is defined as the position of the end of the movable lens relative to the rear end of the lens that is included in the objective lens 230 and is adjacent to the movable lens on the side of the object (see FIG. 9), for example. The details of the operation section 600 and the lens control section 360 are described later.

The control section 340 is bidirectionally connected to the white light source 110, the image processing section 330, and the external I/F section 500, and controls the white light source 110, the image processing section 330, and the external I/F section 500 according to input information output from the external I/F section 500. The external I/F section 500 is an interface that allows the user to perform an input operation or the like on the endoscope system. The external I/F section 500 includes a start button for starting/stopping the imaging operation, an exposure adjustment button for adjusting the brightness of the image, an adjustment button for adjusting the imaging conditions and the image processing parameters, and the like.

Figure 10:
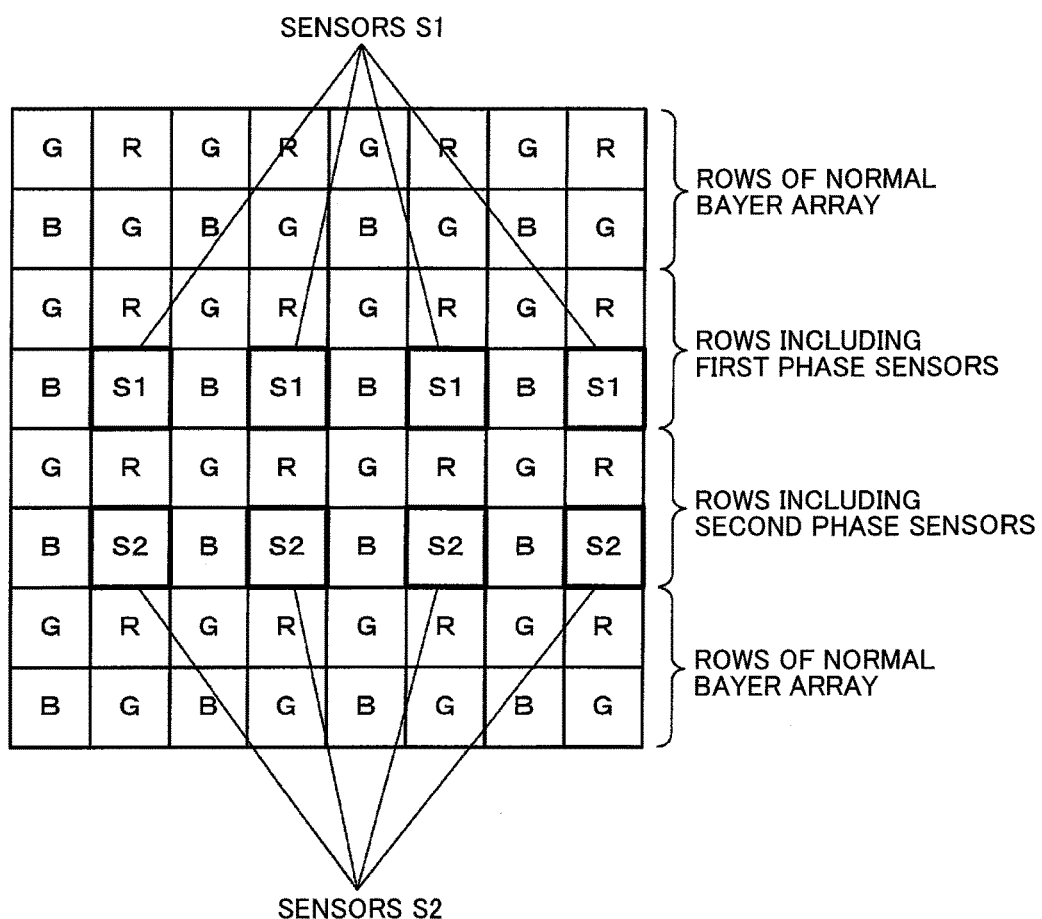
FIG. 10 illustrates a configuration example of an image sensor that includes a phase sensor.

The details of the phase sensors S1 and S2 included in the image sensor 260 (see FIG. 10), and the phase signals output from the phase sensors S1 and S2 are described below. The pixels S1 and S2 (phase sensors S1 and S2) correspond to the functional pixels S1 and S2 disclosed at paragraphs [0074] to [0083] of JP-A-2000-156823, for example. Each of the pixels S1 and S2 (phase sensors S1 and S2) has an opening that is biased from the center of the pixel in the lateral direction. The above configuration achieves an effect similar to that achieved when dividing the pupil of the objective lens 230 in the lateral direction. Therefore, the image signals from a plurality of phase sensors S1 and S2 arranged in the horizontal direction in FIG. 10 are considered to be the phase signals of a light beam that has passed through each pupil. For example, when the position of the object image formed by the objective lens 230 coincides with the image plane of the image sensor (i.e., the object is in focus), the phase signals output from the phase sensors S1 coincide with the phase signals output from the phase sensors S2. When the position of the object image formed by the objective lens 230 is situated in front of (or behind) the image plane of the image sensor (i.e., the object is out of focus), a phase difference occurs between the phase signals output from the phase sensors S1 and the phase signals output from the phase sensors S2. Note that only a pair of phase sensors S1 and S2 may be provided at the center of the imaging section, or a plurality of pairs of phase sensors S1 and S2 may optionally be provided at arbitrary positions of the imaging section, for example.

Figure 11:
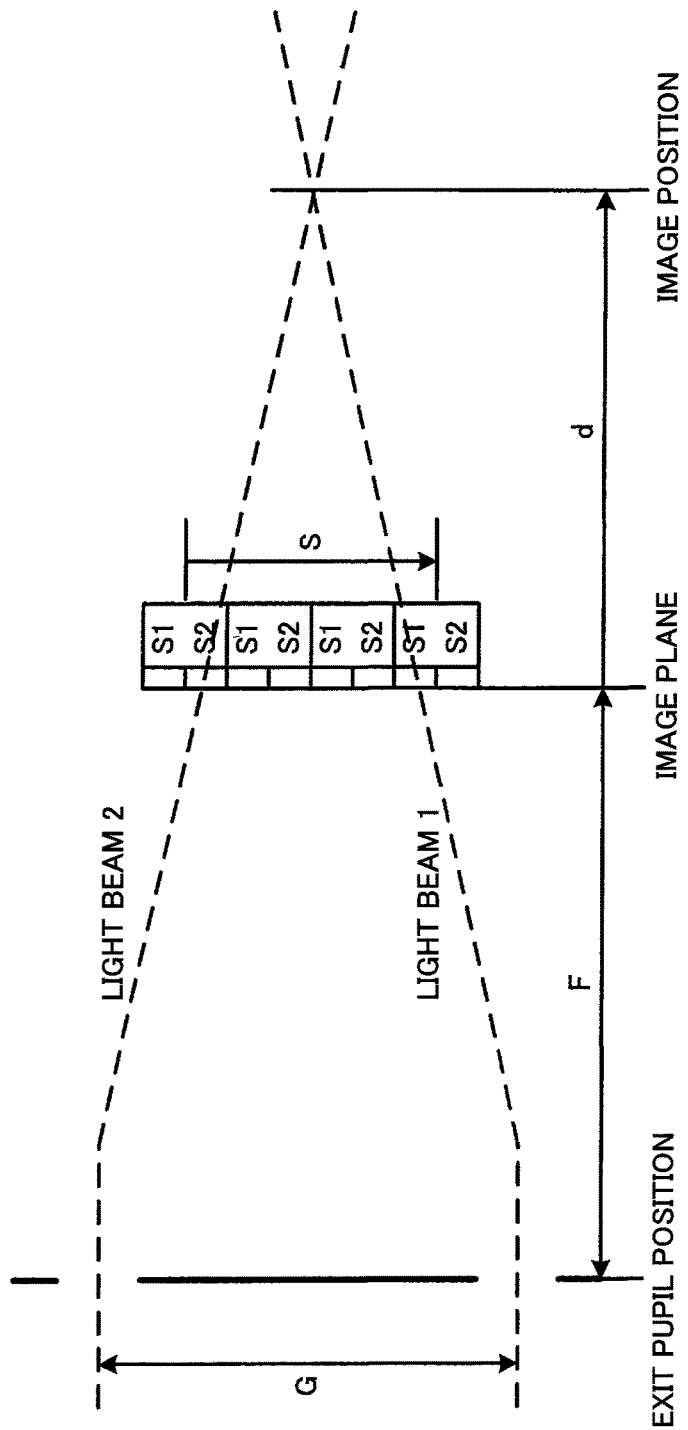
FIG. 11 is a view illustrating light beams that pass through divided pupils, and each parameter.

The moving amount calculation section 350 calculates the moving amount of the movable lens 240 as described below (see FIG. 11). FIG. 11 is a view illustrating light beams that pass through divided pupils when the image position is situated behind the image plane. The light beam 1 is a light beam that has passed through the pupil corresponding to each phase sensor S1, and the light beam 2 is a light beam that has passed through the pupil corresponding to each phase sensor S2. Since the image position is situated at a position differing from the image plane (i.e., a position behind the image plane), a phase difference S occurs between the phase signals output from the phase sensors S1 and the phase signals output from the phase sensors S2. Note that S is a positive or negative vector. The direction indicated by the arrow in FIG. 11 is the positive direction. The phase difference S may be calculated using a known phase detection AF technique. The distance between the image plane and the exit pupil is referred to as F, the distance between the centers of gravity of the divided pupils is referred to as G, and the defocus amount is referred to as d. Note that d is a positive or negative vector. The direction indicated by the arrow in FIG. 11 is the positive direction. In this case, the following expression (1) is satisfied, and the defocus amount d can be calculated using the following expression (2) obtained by transforming the expression (1). Note that the above description is similarly applied to the case where the image position is situated in front of the image plane. The defocus amount d may also be calculated by the method disclosed at paragraphs [0108] to [0110] of JP-A-2000-156823, for example.

$$G/(F+d)=S/d \tag{1}$$

$$d=F\cdot S/(G-S) \tag{2}$$

The moving amount calculation section 350 calculates the moving amount of the movable lens 240 necessary for implementing an in-focus state from the defocus amount d calculated using the expression (2) for the phase signals sequentially output from the phase sensors S1 and S2 in the same cycle as that of the image signals, for example, and sequentially outputs the calculated moving amount to the lens control section 360. For example, the ratio R of the moving amount of the movable lens 240 to the moving amount of the image position may be calculated in advance from the design data of the objective lens 230 using the following expression (3), and the moving amount D may be calculated using the following expression (4).

$$R=\text{moving amount of movable lens/moving amount of image position} \tag{3}$$

$$D=R\cdot d \tag{4}$$

For example, when the ratio R of the moving amount of the movable lens 240 to the moving amount of the image position changes depending on the position x of the movable lens 240, the position xn of the movable lens and the ratio Rn corresponding to the position xn of the movable lens may be stored in advance as a look-up table (LUT) (see FIG. 12), and the ratio Rn corresponding to the position xn of the movable lens 240 at a timing at which the phase signals were output from the phase sensors S1 and S2 may be used as the ratio R in the expression (4) to calculate the moving amount D.

When the distance F between the image plane and the exit pupil and the distance G between the centers of gravity of the pupils (see FIG. 11) also change depending on the position x of the movable lens 240, the distance Fn and the distance Gn corresponding to the position xn of the movable lens 240 are also stored in the LUT (see FIG. 13). The distance Fn and the distance Gn corresponding to the position xn of the movable lens 240 at a timing at which the phase signals were output from the phase sensors S1 and S2 are used as the distance F and the distance G in the expression (2) to calculate the defocus amount dn. The calculated defocus amount dn and the ratio Rn corresponding to the position xn of the movable lens 240 are used as the defocus amount d and the ratio R in the expression (4) to calculate the moving amount D. Note that it is unnecessary to take account of the parameter illustrated in FIG. 13 of which the change depending on the position of the movable lens 240 is negligibly small. Another parameter that may be used to calculate the moving amount and changes to a large extent depending on the position of the movable lens 240 may be added to the LUT.

The moving amount calculation section 350 may calculate and output the moving amount corresponding to all of the phase signals sequentially output from the phase sensors S1 and S2, or may sample the phase signals in an arbitrary cycle, and calculate and output the moving amount, for example. In the latter case, the moving amount is output from the moving amount calculation section 350 in a cycle longer than the image signal output cycle.

Figure 8:
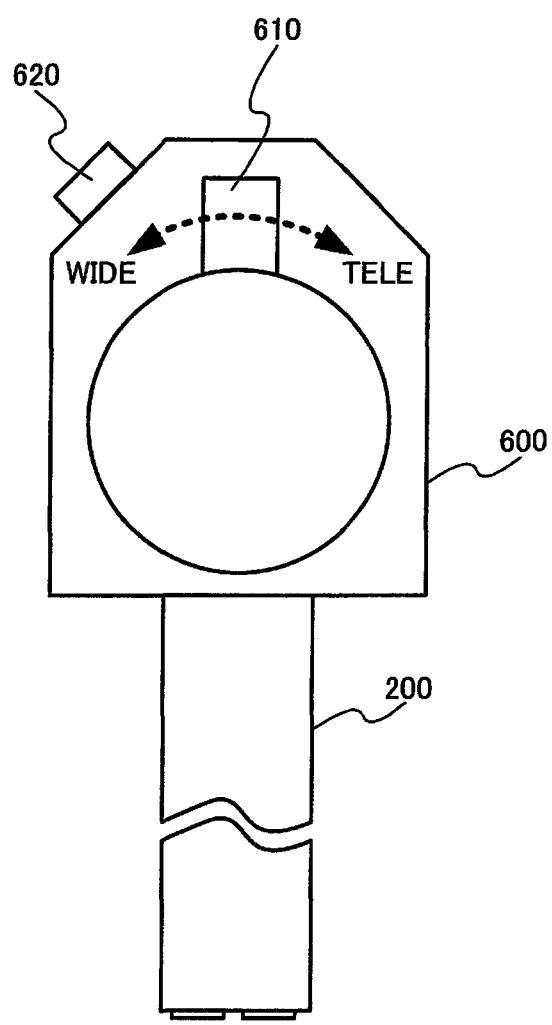
FIG. 8 illustrates a configuration example of an operation section.

The details of the operation section 600, the moving amount calculation section 350, and the lens control section 360 are described below. FIG. 8 illustrates an example of the operation section 600 according to the first embodiment. The operation section 600 according to the first embodiment is integrated with the imaging section 200, for example. The operation section 600 includes a zoom lever 610 and an AF button 620. The zoom lever 610 can be continuously operated within a given range, for example. The user can continuously adjust the position of the movable lens 240 from the WIDE end to the TELE end by moving the zoom lever 610. For example, the operation section 600 outputs position information about the zoom lever 610 to the lens control section 360. The lens control section 360 links the position information about the zoom lever 610 to the position information about the movable lens 240 using a look-up table set in advance or the like, and outputs the position information about the movable lens 240 to the lens driver section 250. The lens driver section 250 drives the movable lens 240 based on the position information output from the lens control section 360. The operation section 600 alternately outputs an AF start/stop signal to the lens control section 360 each time the AF button 620 has been pressed, for example.

Figure 4:
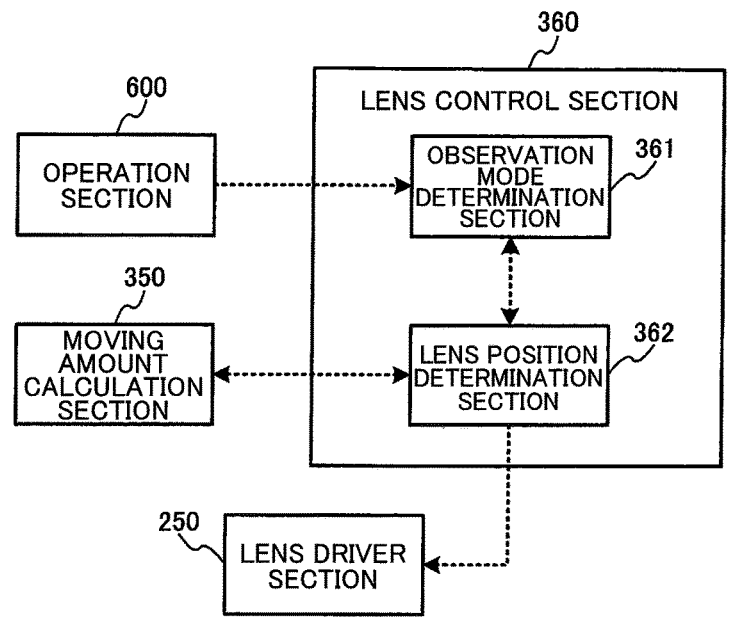
FIG. 4 illustrates a configuration example of a lens control section according to the first embodiment.

FIG. 4 illustrates an example of the lens control section 360 according to the first embodiment. The lens control section 360 includes an observation mode determination section 361 and a lens position determination section 362. The observation mode determination section 361 determines the observation mode based on AF start/stop information output from the operation section 600, and outputs observation mode information to the lens position determination section 362. Specifically, the observation mode determination section 361 selects the fixed focus mode when the AF start signal is not output from the operation section 600, and selects the AF mode when the AF start signal has been output from the operation section 600. The lens position determination section 362 outputs the position information about the movable lens 240 that is linked to the position information about the zoom lever 610 to the lens driver section 250 when the fixed focus mode has been selected by the observation mode determination section 361. The lens driver section 250 adjusts the position of the movable lens 240 based on the position information output from the lens position determination section 362.

Figure 7:
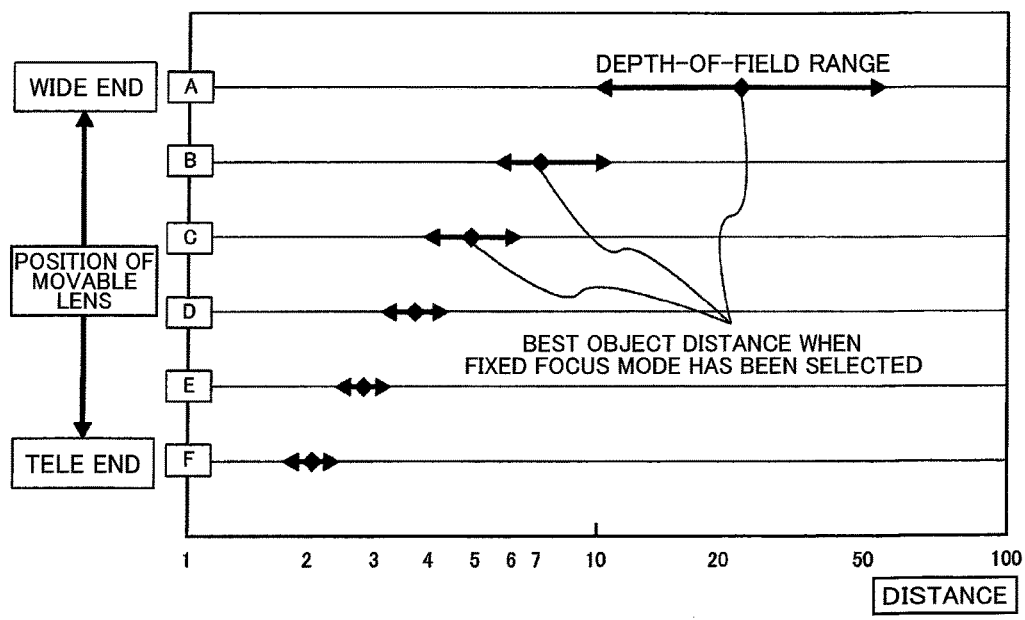
FIG. 7 is a view illustrating the relationship between the position of a movable lens, the best object distance, and the depth-of-field range when a fixed focus mode has been selected.

FIG. 7 illustrates the position of the movable lens 240, the best object distance, and the depth-of-field range when the fixed focus mode has been selected. In the first embodiment, the position of the movable lens 240 can be continuously moved by operating the zoom lever 610. Note that FIG. 7 illustrates the case where the position of the movable lens 240 is moved stepwise for convenience of explanation. In the first embodiment, when the fixed focus mode has been selected, the position of the movable lens 240 is controlled so that the best object distance and the depth of field similar to those of a known endoscope system having a zoom function are implemented by operating the zoom lever.

The lens position determination section 362 calculates the position information about the movable lens 240 after movement based on the moving amount output from the moving amount calculation section 350 when the AF mode has been selected by the observation mode determination section 361, and outputs the calculated position information to the lens driver section 250. The lens driver section 250 adjusts the position of the movable lens 240 based on the position information output from the lens position determination section 362. The above operation makes it possible to bring the object into focus by adjusting the position of the movable lens when the AF mode has been selected.

The lens position determination section 362 may stop the AF operation after performing the focus operation once, or may continue the AF operation until the AF stop signal is output from the observation mode determination section 361. When it is desired to continue the AF operation, the lens position determination section 362 sequentially outputs the position information about the movable lens 240 corresponding to the moving amount cyclically output from the moving amount calculation section 350 to the lens driver section 250. The lens driver section 250 adjust the position of the movable lens 240 based on the position information sequentially output from the lens position determination section 362. The above operation makes it possible for the endoscope system according to the first embodiment to continuously bring the object into focus so as to follow the object even when the object distance has changed. Since the endoscope system according to the first embodiment can implement the zoom function and the continuous AF operation using a single movable lens, it is possible to implement a reduction in size and cost of the imaging section.

In the first embodiment, since the angle of view also changes depending on the position of the movable lens 240, the image may flicker, and observation may be hindered when the focus operation is performed in the same cycle as that of the image signals. In this case, the moving amount calculation section 350 may sample the phase signals in an arbitrary cycle, and output the moving amount to the lens position determination section 362 in the cycle after sampling. The above configuration makes it possible for the endoscope system according to the first embodiment to perform the focus operation in an arbitrary cycle, and continuously bring the object into focus so as to follow the object while suppressing a situation in which the image flickers.

According to the first embodiment, the imaging device includes an imaging optical system that includes the movable lens 240 that simultaneously adjusts the angle of view and the in-focus object distance, the image sensor 260, a plurality of phase sensors (S1 and S2 in FIG. 10), an acquisition section (corresponding to the AID conversion section 320) that acquires phase information from the plurality of phase sensors, the lens control section 360 that controls the position of the movable lens 240, and the moving amount calculation section 350 that calculates the moving amount of the movable lens 240 necessary for implementing an in-focus state based on the phase difference calculated from the phase information acquired by the acquisition section (see FIG. 1). The lens control section 360 controls the position of the movable lens 240 based on the moving amount calculated by the moving amount calculation section 350. Note that the in-focus state refers to the in-focus state of an image formed on the image sensor 260 due to light beams that have passed through the imaging optical system.

The imaging optical system according to the first embodiment has the configuration illustrated in FIG. 9, for example. The angle of view and the in-focus object distance are simultaneously adjusted by driving the movable lens 240. The movable lens 240 consists of one lens, or consists of a plurality of lenses. The expression "the angle of view and the in-focus object distance are simultaneously adjusted" used herein means that both the angle of view and the in-focus object distance are changed by moving the movable lens 240. The term "in-focus object distance" used herein refers to the distance from the imaging optical system to the object when the object image that is formed by light incident on the image sensor 260 through the imaging optical system is in focus. Even if the light does not converge at one point on the image sensor 260, it is considered that the object image is in focus when the size of the light is smaller than the permissible circle of confusion. Therefore, the in-focus object distance has a certain range. The in-focus object distance may be a value having such a range. Note that the in-focus object distance refers to the best object distance in a narrow sense. The term "best object distance" used herein refers to the distance from the imaging optical system to the object when light incident on the image sensor 260 through the imaging optical system converges within a minimum area on the image sensor 260.

The above configuration makes it possible to appropriately implement the focus control operation (AF (autofocus) operation) even when using the lens configuration (single-group-drive lens configuration) illustrated in FIG. 9. The contrast AF operation that is widely used changes the focus little by little to acquire a plurality of contrast values, and calculates the maximum value among the acquired contrast values. However, since the angle of view changes along with a change in focus when employing the single-group-drive lens configuration, the acquired image may flicker. In particular, the image may significantly flicker when using the continuous AF operation. According to the first embodiment, a situation in which the acquired image flickers is suppressed by performing the focus control operation (phase detection AF operation) that utilizes the phase information from the phase sensors.

The moving amount calculation section 350 may calculate the moving amount of the movable lens 240 based on the phase information from the phase sensors, and the position of the movable lens 240 at a timing at which the phase information was acquired.

The above configuration makes it possible to calculate the moving amount taking account of the phase information and the position of the movable lens 240 at a timing at which the phase information was acquired. The focus control operation based on the phase information refers to the phase detection AF operation in a narrow sense. The phase detection AF operation divides the pupil, and calculates the shift of the image from each divided pupil as the phase difference. The term "pupil" refers to the aperture image viewed from the outside of the optical system. In the first embodiment, the exit pupil (i.e., the pupil viewed from the side of the image) is mainly taken into consideration. As illustrated in FIG. 11, the light beam from the object appears to be emitted from the position of the exit pupil when viewed from the side of the image. Since the pupil is virtually set based on the optical conditions, the position of the pupil and the like may change when the position of the movable lens 240 changes. Therefore, it is desirable to use the optical situation (particularly the position of the movable lens 240) during the focus operation in addition to the phase information in order to appropriately implement the focus control operation.

The moving amount calculation section 350 may change one or more parameters based on the position of the movable lens 240 at a timing at which the phase information was acquired. The moving amount calculation section 350 may calculate the moving amount of the movable lens 240 based on the parameter that has been changed and the phase information. Specifically, at least one of distance information about the distance from the image sensor 260 to the pupil position, center-of-gravity distance information about the divided pupils, and ratio information about the ratio of the moving amount to the distance from the image sensor 260 to the image position may be used as the parameter.

The above configuration makes it possible to change the parameter based on the position of the movable lens 240, and calculate the moving amount using the parameter. The term "parameter" used herein refers to data that is necessary when calculating the moving amount D of the movable lens 240 from the phase information. In particular, the term "parameter" used herein refers to data that changes in value corresponding to the position of the movable lens 240. In the first embodiment, the shift between the image acquired by the phase sensors S1 and the image acquired by the phase sensors S2 is acquired as the phase difference S (see FIG. 11), and the moving amount D of the movable lens 240 is calculated from the acquired phase difference S, for example. In the example illustrated in FIG. 11, it is necessary to calculate the distance d from the image plane to the image position using the distance F from the image plane to the exit pupil position and the distance G between the centers of gravity of the pupils, and acquire the ratio R in order to implement conversion from the defocus amount d to the moving amount D. The distance F, the distance G, and the ratio R may change corresponding to the position of the movable lens 240, the distance F, the distance G, and the ratio R may be used as the parameter. The distance F, the distance G, the ratio R, and the like may be expressed as a function of the position x of the movable lens 240, or may be stored in a look-up table (see FIG. 13). Note that the above parameters are merely examples, and the moving amount may be calculated using a parameter other than the above parameters.

The imaging optical system may be an optical system that is configured so that the angle of view and the in-focus object distance monotonously decrease as the movable lens 240 moves from the wide-angle end to the telescopic end.

The above configuration makes it possible to implement the imaging optical system illustrated in FIG. 7. The in-focus object distance (best object distance) decreases as the position of the movable lens 240 is moved from the wide-angle side to the telescopic side. Specifically, the depth-of-field range is set at a position closer to the imaging optical system (i.e., the object positioned close to the imaging optical system is brought into focus). In particular, it is considered that zoom observation is performed using the endoscope apparatus or the like when the movable lens 240 is moved to the telescopic side (i.e., the zoom magnification is increased). In this case, the end of the insertion section (imaging section 200) is normally moved closer to the object (observation target) to further zoom in the object. Specifically, since it is considered that the distance between the imaging optical system and the object decreases as the position of the movable lens 240 is moved to the telescopic side, it is easy to bring the object into focus by utilizing the optical system illustrated in FIG. 7.

The acquisition section may acquire the phase information from the phase sensors provided in the array of pixels of the image sensor.

The above configuration makes it possible to use an image sensor having the configuration illustrated in FIG. 10. When the phase sensor is provided separately from the image sensor, it is necessary to provide a lens for causing the reflected light from the object to be incident on the phase sensor. Therefore, the configuration of the imaging optical system becomes complex, and it is difficult to reduce the size of the imaging optical system. Moreover, the cost of the imaging optical system increases. In particular, the size of the insertion section of the endoscope apparatus increases when the imaging optical system has a large size. Therefore, it is desirable to reduce the size and the cost of the imaging optical system by utilizing the configuration illustrated in FIG. 10.

The lens control section 360 may control the position of the movable lens 240 in a cycle equal to the cycle in which the acquisition section acquires the image information from the image sensor. Alternatively, the lens control section 360 may control the position of the movable lens 240 in a cycle longer than the cycle in which the acquisition section acquires the image information from the image sensor.

The above configuration makes it possible to make the rate of controlling the position of the movable lens 240 equal to the image information acquisition rate, or make the rate of controlling the position of the movable lens 240 lower than the image information acquisition rate. Since the phase information is acquired at the same timing as the image information acquisition timing, it is possible to control the position of the movable lens 240 in the same cycle as the image information acquisition cycle. In this case, since the focus control operation is performed at a high rate, it is possible to increase the possibility that the object is in focus. When the image information acquisition rate is high, for example, it may be difficult for the lens driver section 250 to mechanically control the position of the movable lens 240 at the same rate as the image information acquisition rate. When the position of the movable lens 240 is controlled at a high rate, the position of the movable lens 240 may frequently change, and flickers may occur when using the single-group-drive lens configuration. In this case, the position of the movable lens 240 may be controlled in a cycle longer than the image information acquisition cycle. In such a case, an image for which focus control is insufficient may be generated depending on the image information. However, since the control process performed by the lens driver section 250 is facilitated, and it is unnecessary to perform the process on all of the acquired phase information, the processing load can be reduced. Moreover, since frequent movement of the movable lens 240 can be suppressed, it is possible to suppress a situation in which the image flickers.

The lens control section 360 may perform the continuous AF operation to control the position of the movable lens 240.

The above configuration makes it possible to perform the continuous AF operation as the AF operation. It is effective to perform the continuous focus control operation using the continuous AF operation when acquiring a movie. In particular, it is likely that the image acquired by the endoscope apparatus is a movie in order to perform efficient in vivo observation. When using the single-group-drive lens configuration, it is difficult to implement the continuous AF operation since the effects of flickers become significant. However, since the effects of flickers can be suppressed by the method according to the first embodiment, it is possible to effectively implement the continuous AF operation.

When a reference point is set at a position between the wide-angle end and the telescopic end within the moving range of the movable lens, the lens control section 360 may control the position of the movable lens based on the moving amount calculated by the moving amount calculation section 350 when the movable lens is situated on the telescopic side relative to the reference point.

The position of the movable lens 240 is controlled (i.e., focus control/AF operation) when the movable lens 240 is situated on the telescopic side relative to the reference point. The AF operation may or may not be performed when the movable lens 240 is situated on the wide-angle side relative to the reference point. Since it is considered that the depth of field is deep when the movable lens 240 is situated on the wide-angle side relative to the reference point as compared with the case where the movable lens 240 is situated on the telescopic side relative to the reference point, and the user can manually adjust the focus, the AF operation may not be performed when the movable lens 240 is situated on the wide-angle side relative to the reference point. In this case, the observation mode determination section 361 may acquire the position of the movable lens 240, and the lens control section 360 may select the fixed focus mode when the movable lens 240 is situated on the wide-angle side relative to the reference point, and select the AF mode when the movable lens 240 is situated on the telescopic side relative to the reference point, for example.

The above configuration makes it possible to determine whether or not to perform the focus operation (AF operation) based on the position of the movable lens 240. In the above example, the AF operation starts when the user operates the AF button 620 illustrated in FIG. 8. Specifically, the user must determine whether or not to perform the AF operation. If whether or not to perform the AF operation can be determined based on the position of the movable lens 240, it is unnecessary for the user to determine whether or not to perform the AF operation, and it is unnecessary to operate the AF button 620 or the like when performing the AF operation. Therefore, it is possible to implement a user-friendly system. The AF operation is performed when the movable lens 240 is situated on the telescopic side relative to the reference point since the depth of field becomes shallow as the movable lens 240 moves toward the telescopic side (as the zoom magnification increases), and it becomes difficult to manually bring the object into focus. When using the lens having the configuration illustrated in FIG. 7, the best object distance decreases as the movable lens 240 moves toward the telescopic side. Since the depth of field also decreases as the best object distance decreases, it becomes more difficult to manually bring the object into focus when using the lens having the configuration illustrated in FIG. 7. Therefore, it is advantageous to perform the AF operation.

The first embodiment may also be applied to an endoscope apparatus that includes an imaging optical system that includes the movable lens 240 that simultaneously adjusts the angle of view and the in-focus object distance, an acquisition section (corresponding to the A/D conversion sections 310 and 320) that acquires the image information from the image sensor 260 and the phase information from the phase sensors, the lens control section 360 that controls the position of the movable lens 240, and the moving amount calculation section 350 that calculates the moving amount of the movable lens 240 based on the phase information acquired by the acquisition section. The lens control section 360 controls the position of the movable lens 240 based on the moving amount calculated by the moving amount calculation section 350.

The above configuration makes it possible to implement the process according to the first embodiment using the endoscope apparatus instead of the imaging device. Since the imaging section 200 of the endoscope apparatus is inserted into a body, it is preferable to reduce the size of the imaging section 200. Therefore, it is advantageous to use a simple single-group-drive lens configuration (FIG. 9). Since the endoscope apparatus may be used to find/observe a lesion area, and perform procedures on tissue using a tool, it is necessary to minimize a situation in which the image presented to the user (doctor) flickers. Since the size of the imaging section 200 can be reduced while suppressing a situation in which the image flickers by utilizing the method according to the first embodiment, it is possible to implement an endoscope apparatus that is preferable for the doctor and the subject.

3. Second Embodiment

An imaging device according to the second embodiment and an endoscope system including the same are described below with reference to FIG. 2.

A processing section 300 according to the second embodiment includes an A/D conversion sections 310 and 320, an image processing section 330, a control section 340, a moving amount calculation section 350, a lens control section 360, a contrast value calculation section 370, and a defocus index calculation section 380. The A/D conversion section 310 converts analog image signals output from the image sensor 260 into digital image signals, and outputs the digital image signals to the image processing section 330 and the contrast value calculation section 370. The contrast value calculation section 370 detects a high-frequency component of the image signals output from the A/D conversion section 310 to calculate a contrast value, and outputs the contrast value to the lens control section 360, for example.

The A/D conversion section 320 converts analog phase signals output from the phase sensors S1 and S2 included in the image sensor 260 into digital phase signals, and outputs the digital phase signals to the defocus index calculation section 380. The defocus index calculation section 380 detects a high-frequency component of the phase signals output from the A/D conversion section 320 to calculate a defocus index, and outputs the defocus index to the lens control section 360, for example. The term "defocus index" used herein refers to an index that indicates the degree of defocus of the phase signal. The defocus index decreases, and the amount of high-frequency component decreases as the phase signal becomes out of focus. The defocus index calculation section 380 outputs the phase signals output from the A/D conversion section 320 directly to the moving amount calculation section 350. The remaining configuration is the same as described above in connection with the first embodiment.

Figure 5:
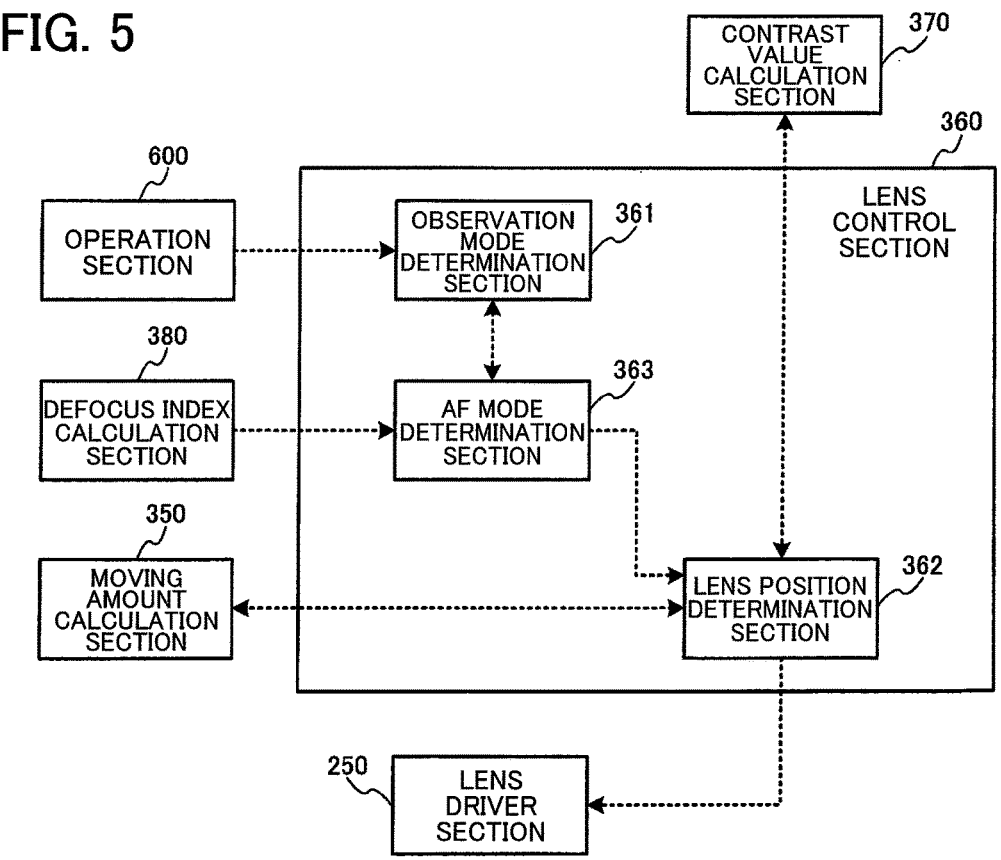
FIG. 5 illustrates a configuration example of a lens control section according to the second embodiment.

The details of the lens control section 360 according to the second embodiment are described below with reference to FIG. 5. The lens control section 360 according to the second embodiment includes an observation mode determination section 361, a lens position determination section 362, and an AF mode determination section 363. The observation mode determination section 361 determines the observation mode based on the AF start/stop information output from the operation section 600, and outputs observation mode information to the AF mode determination section 363. Specifically, the observation mode determination section 361 selects the fixed focus mode when the AF start signal is not output from the operation section 600, and selects the AF mode when the AF start signal has been output from the operation section 600 in the same manner as in the first embodiment. The AF mode determination section 363 selects the fixed focus mode when the observation mode determination section 361 has selected the fixed focus mode, and outputs information about the selected mode to the lens position determination section 362. The AF mode determination section 363 determines the AF mode using the defocus index output from the defocus index calculation section 380 when the observation mode determination section 361 has selected the AF mode, and outputs AF mode information to the lens position determination section 362. For example, the AF mode determination section 363 selects a contrast AF mode when the defocus index output from the defocus index calculation section 380 is equal to or smaller than a threshold value, and selects a phase detection AF mode when the defocus index output from the defocus index calculation section 380 is equal to or larger than the threshold value.

When the AF mode determination section 363 has selected the fixed focus mode or the phase detection AF mode, the lens position determination section 362 operates in the same manner as in the first embodiment when the fixed focus mode or AF mode has been selected. When the AF mode determination section 363 has selected the contrast AF mode, the lens position determination section 362 performs the focus operation by controlling the movable lens 240 in the same manner as a known contrast AF technique based on the contrast value output from the contrast value calculation section 370. This is because it is difficult to calculate the phase difference when the degree of defocus of the phase signal is high (i.e., when the defocus index is small). It is possible to reliably bring the object into focus by performing the above control process. When the object has been brought into focus by performing the contrast AF operation, the defocus index calculated by the defocus index calculation section 380 sufficiently increases, and the AF mode determination section 363 selects the phase detection AF mode. Therefore, the lens position determination section 362 operates in the same manner as in the first embodiment when the AF mode has been selected, and the object can be continuously brought into focus so as to follow the object. The above configuration makes it possible to continue the focus operation when the AF operation has started, or when the image has been significantly defocused during the AF operation.

Figure 2:
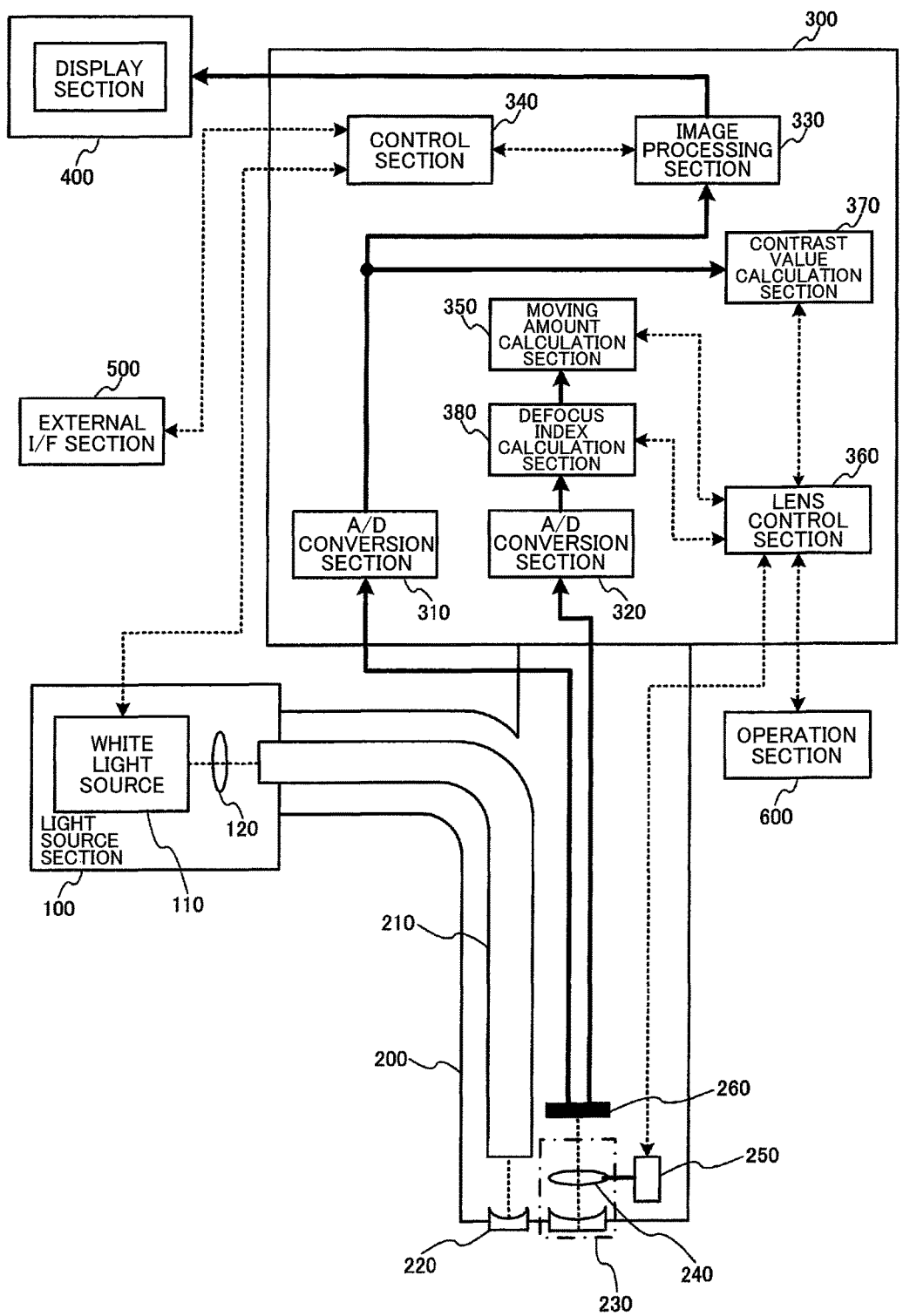
FIG. 2 illustrates a configuration example of an imaging device according to a second embodiment and an endoscope apparatus including the same.

According to the second embodiment, the imaging device includes the contrast value calculation section 370 that calculates the contrast value included in the image information (see FIG. 2). The lens control section 360 selectively controls a phase mode that controls the position of the movable lens 240 based on the phase information and a contrast mode that controls the position of the movable lens 240 based on the contrast value.

The above configuration makes it possible to selectively control the position of the movable lens 240 using phase information (i.e., phase mode (phase detection AF operation in a narrow sense)), or control the position of the movable lens 240 using the contrast value (i.e., contrast mode (contrast AF operation in a narrow sense)). Specifically, the phase mode or the contrast mode can be used depending on the situation. Note that it is undesirable to use the contrast mode when using the single-group-drive lens configuration since the image may flicker (refer to the first embodiment), for example. Therefore, the contrast mode may be used when the phase mode is not effective, and the phase mode may be used when the phase mode is effective.

The imaging device may include the defocus index calculation section 380 that calculates the defocus index that indicates the degree of defocus of the image indicated by the image information (see FIG. 2). The lens control section 360 may switch the mode between the phase mode and the contrast mode based on the defocus index.

The above configuration makes it possible to switch the mode between the phase mode and the contrast mode based on the defocus index. In the phase mode (phase detection AF mode in a narrow sense), a shift between a plurality of images from different exit pupils (phase difference in a narrow sense) may be used. Specifically, the phase mode is not effective when the plurality of images are defocused to such an extent that a shift between the plurality of images cannot be determined. When the signal distribution (signal waveform) has a characteristic feature (e.g., when the signal values of the phase signals from the phase sensors differ depending on the position), a spatial shift between a first image formed by light from a first exit pupil and a second image formed by light from a second exit pupil can be easily determined. However, when the degree of defocus is large, the difference of the maximum peak and the minimum peak of the signal values is small (i.e., a flat signal waveform is obtained). In this case, it is difficult to determine the degree of positional shift. It is difficult to perform the focus control operation based on the phase information in such a situation. Therefore, the mode can be effectively switched between the phase mode and the contrast mode by utilizing the defocus index. More specifically, the contrast mode may be used when it has been determined that the degree of defocus is large based on the defocus index, and the phase mode may be used when it has been determined that the degree of defocus is small based on the defocus index.

The defocus index calculation section 380 may calculate the defocus index based on the phase information output from the phase sensors.

The above configuration makes it possible to calculate the defocus index from the phase information. Since the phase information also indicates the signals that indicate the image of the object, the degree of defocus can be determined based on the signal values. Specifically, whether or not the signal waveform is flat may be determined. For example, a high-frequency component may be extracted from the phase information, and may be used as the defocus index.

4. Third Embodiment

Figure 3:
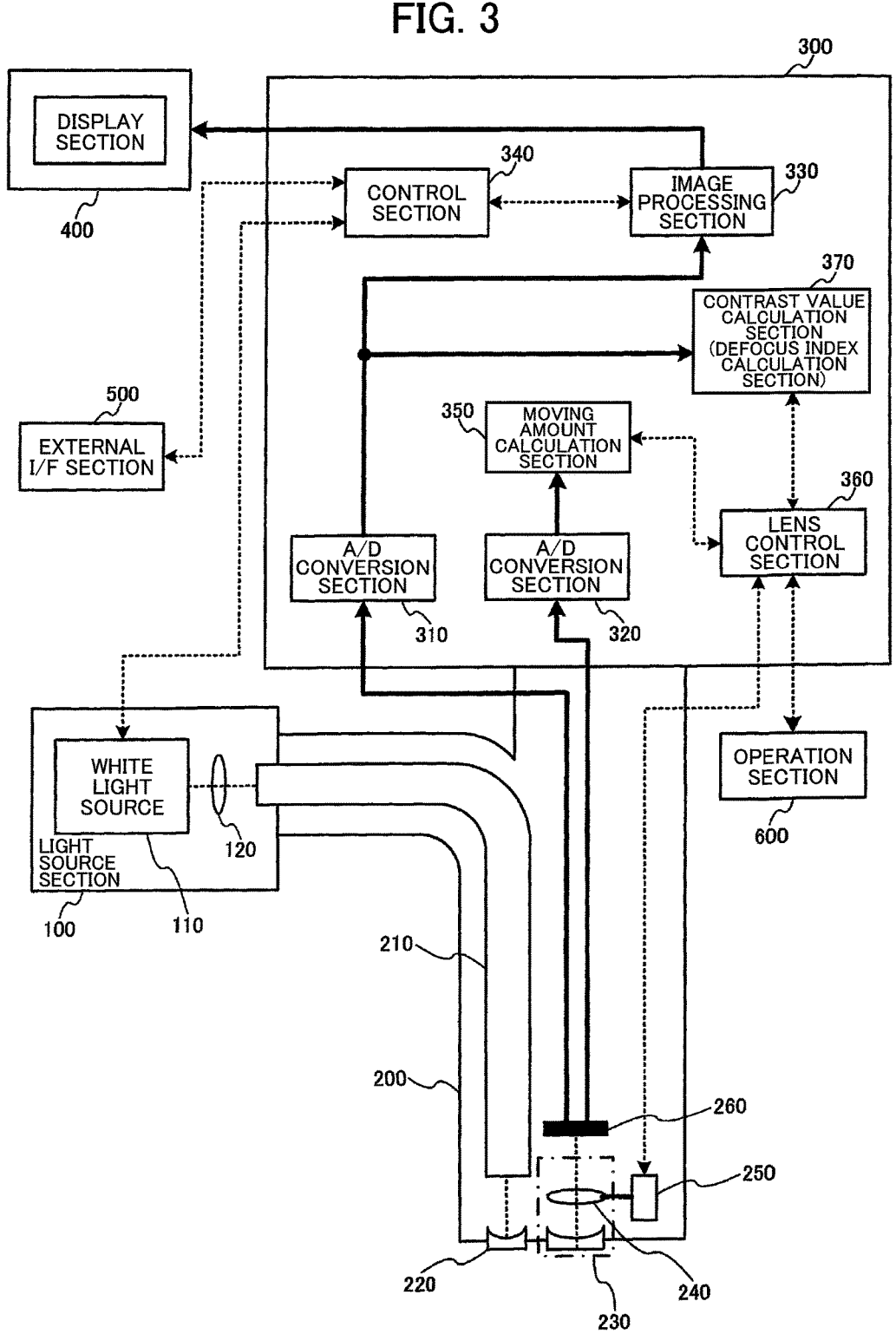
FIG. 3 illustrates a configuration example of an imaging device according to a third embodiment and an endoscope apparatus including the same.

An imaging device according to the third embodiment and an endoscope system including the same are described below with reference to FIG. 3.

A processing section 300 according to the third embodiment includes A/D conversion sections 310 and 320, an image processing section 330, a control section 340, a moving amount calculation section 350, a lens control section 360, and a contrast value calculation section 370. In the third embodiment, the contrast value calculation section 370 also serves as a defocus index calculation section (corresponding to the defocus index calculation section 380 illustrated in FIG. 2) (see FIG. 3). Specifically, the third embodiment differs from the second embodiment in that the contrast value is used as the defocus index instead of the phase information (described later).

The A/D conversion section 310 converts analog image signals output from the image sensor 260 into digital image signals, and outputs the digital image signals to the image processing section 330 and the contrast value calculation section 370. The contrast value calculation section 370 detects a high-frequency component of the image signals output from the A/D conversion section 310 to calculate a contrast value, and outputs the contrast value to the lens control section 360, for example. The contrast value is an index that indicates the degree of defocus of the image signal. The contrast value decreases as the image signal becomes of out of focus, and the amount of high-frequency component decreases. The remaining configuration is the same as described above in connection with the first embodiment.

Figure 6:
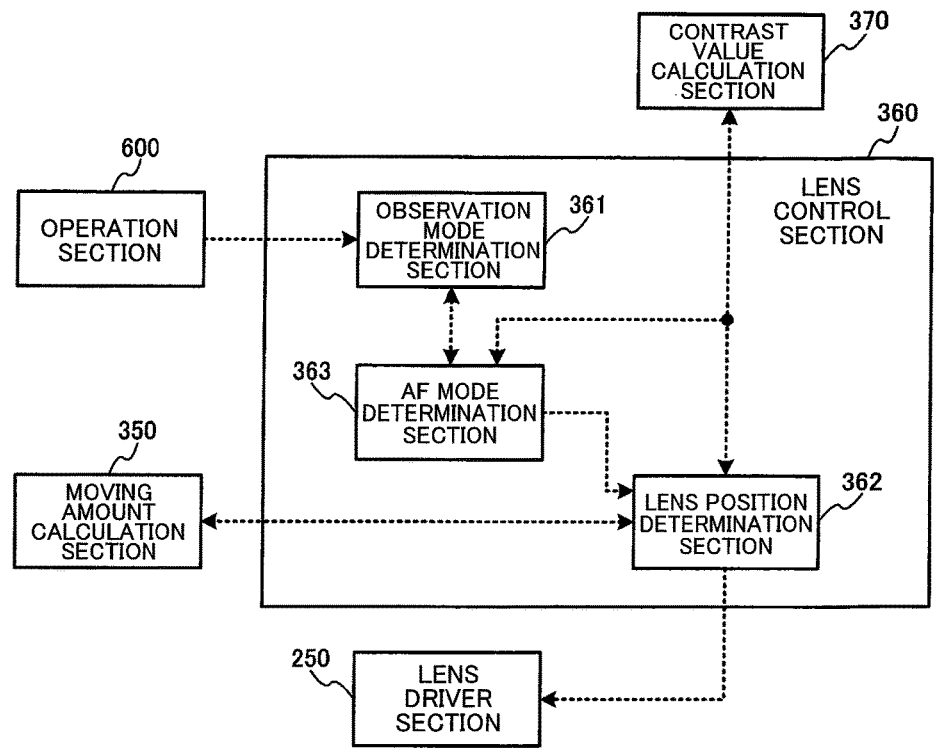
FIG. 6 illustrates a configuration example of a lens control section according to the second embodiment.

The details of the lens control section 360 according to the third embodiment are described below with reference to FIG. 6. The lens control section 360 according to the third embodiment includes an observation mode determination section 361, a lens position determination section 362, and an AF mode determination section 363. The observation mode determination section 361 determines the observation mode based on the AF start/stop information output from the operation section 600, and outputs observation mode information to the AF mode determination section 363. Specifically, the observation mode determination section 361 selects the fixed focus mode when the AF start signal is not output from the operation section 600, and selects the AF mode when the AF start signal has been output from the operation section 600 in the same manner as in the first embodiment. The AF mode determination section 363 selects the fixed focus mode when the observation mode determination section 361 has selected the fixed focus mode, and outputs information about the selected mode to the lens position determination section 362. The AF mode determination section 363 determines whether the AF mode is the contrast AF mode or the phase detection AF mode using the contrast value output from the contrast value calculation section 370 when the observation mode determination section 361 has selected the AF mode, and outputs the AF mode information to the lens position determination section 362. For example, the AF mode determination section 363 selects the contrast AF mode when the contrast value output from the contrast value calculation section 370 is equal to or smaller than a threshold value, and selects the phase detection AF mode when the contrast value output from the contrast value calculation section 370 is equal to or larger than the threshold value.

When the AF mode determination section 363 has selected the fixed focus mode or the phase detection AF mode, the lens position determination section 362 operates in the same manner as in the first embodiment when the fixed focus mode or AF mode has been selected. When the AF mode determination section 363 has selected the contrast AF mode, the lens position determination section 362 performs the focus operation by controlling the movable lens 240 in the same manner as a known contrast AF technique based on the contrast value output from the contrast value calculation section 370. This is because it is difficult to calculate the phase difference when the degree of defocus of the phase signal is high. It is possible to reliably bring the object into focus by performing the above control process. In the third embodiment, the degree of defocus of the phase signal is determined using the contrast value since the contrast value is correlated with the degree of defocus of the phase signal. When the object has been brought into focus by performing the contrast AF operation, the contrast value sufficiently increases, and the AF mode determination section 363 selects the phase detection AF mode. Therefore, the lens position determination section 362 operates in the same manner as in the first embodiment when the AF mode has been selected, and the object can be continuously brought into focus so as to follow the object. The above configuration makes it possible to continue the focus operation when the AF operation has started, or when the image has been significantly defocused during the AF operation.

According to the third embodiment, a defocus index calculation section (corresponding to the contrast value calculation section 370 (see FIG. 3)) calculates the defocus index based on the contrast value calculated by the contrast value calculation section 370.

The above configuration makes it possible to calculate the defocus index from the contrast value. The contrast value is calculated from a high-frequency component of the image, and may be used to determine the degree of in-focus, for example. Therefore, the degree of defocus can be calculated from the contrast value. More specifically, the contrast value may be used directly as the defocus index.

The imaging device and the like according to the embodiments of the invention may include a processor and a memory. The processor may be a central processing unit (CPU), for example. Note that the processor is not limited to a CPU. Various types of processors such as a graphics processing unit (GPU) and a digital signal processor (DSP) may also be used. The processor may be a hardware circuit such as an application specific integrated circuit (ASIC). The memory stores a computer-readable instruction. Each section of the imaging device and the like according to the embodiments of the invention is implemented by causing the processor to execute the instruction. The memory may be a semiconductor memory (e.g., SRAM or DRAM), a register, a hard disk, or the like. The instruction may be an instruction included in an instruction set of a program, or may be an instruction that causes a hardware circuit of the processor to operate.

The first to third embodiments according to the invention and the modifications thereof have been described above. Note that the invention is not limited to the first and to third embodiments and the modifications thereof. Various modifications and variations may be made without departing from the scope of the invention. A plurality of elements described in connection with the first to third embodiments and the modifications thereof may be appropriately combined to implement various configurations. For example, an arbitrary element may be omitted from the elements described in connection with the first to third embodiments and the modifications thereof. Some of the elements described above in connection with different embodiments or modifications thereof may be appropriately combined. Any term cited with a different term having a broader meaning or the same meaning at least once in the specification and the drawings can be replaced by the different term in any place in the specification and the drawings. Specifically, various modifications and applications are possible without materially departing from the novel teachings and advantages of the invention.

What is claimed is:

1. An imaging device comprising:
   an imaging optical system that includes a plurality of lens groups each having at least one lens, wherein a single lens group from among the plurality of lens groups is a movable lens group, and wherein the imaging optical system is configured so that an in-focus object distance is changed along with a change in angle of view;
   an image sensor;
   a plurality of phase sensors;
   an acquisition section that acquires phase information from the plurality of phase sensors;
   a lens control section that controls a position of the movable lens group; and
   a moving amount calculation section that calculates a moving amount of the movable lens group necessary for implementing an in-focus state of an object image of an object formed on the image sensor due to light beams that have passed through the imaging optical system, based on a phase difference that is based on the phase information acquired by the acquisition section,
   wherein:
   the imaging optical system is an optical system that is configured so that the angle of view and the in-focus object distance monotonously decrease as the movable lens group moves from a wide-angle end to a telescopic end,
   the in-focus object distance is a distance from the imaging optical system to the object when the object image is in the in-focus state,
   the moving amount calculation section changes at least one parameter for calculating the moving amount of the movable lens group based on the position of the movable lens group, and calculates the moving amount of the movable lens group based on the at least one parameter having been changed and the phase information, the at least one parameter being selected from among parameters including (i) distance information about a distance from the image sensor to a pupil position, (ii) center-of-gravity distance information about divided pupils, and (iii) ratio information about a ratio of the moving amount to a distance from the image sensor to an image position, and
   the lens control section controls the position of the movable lens group based on the moving amount calculated by the moving amount calculation section.

2. The imaging device as defined in claim 1, wherein the moving amount calculation section calculates the moving amount of the movable lens group based on (i) the phase information from the plurality of phase sensors, and (ii) the position of the movable lens group at a timing at which the phase information was acquired.

3. The imaging device as defined in claim 1, further comprising:
   a contrast value calculation section that calculates a contrast value based on image information,
   wherein the lens control section switches a mode between a phase mode that controls the position of the movable lens group based on the phase information and a contrast mode that controls the position of the movable lens group based on the contrast value.

4. The imaging device as defined in claim 3, further comprising:
   a defocus index calculation section that calculates a defocus index that indicates a degree of defocus of an image indicated by the image information,
   wherein the lens control section switches the mode between the phase mode and the contrast mode based on the defocus index.

5. The imaging device as defined in claim 4, wherein the defocus index calculation section calculates the defocus index based on the phase information output from the plurality of phase sensors.

6. The imaging device as defined in claim 4, wherein the defocus index calculation section calculates the defocus index based on the contrast value calculated by the contrast value calculation section.

7. The imaging device as defined in claim 1, wherein the acquisition section acquires the phase information from the plurality of phase sensors which are provided in an array of pixels of the image sensor.

8. The imaging device as defined in claim 1, wherein the lens control section controls the position of the movable lens group in a cycle equal to a cycle in which the acquisition section acquires image information from the image sensor.

9. The imaging device as defined in claim 1, wherein the lens control section controls the position of the movable lens group in a cycle longer than a cycle in which the acquisition section acquires image information from the image sensor.

10. The imaging device as defined in claim 1, wherein the lens control section performs a continuous autofocus (AF) operation to control the position of the movable lens group.

11. The imaging device as defined in claim 1, wherein the lens control section controls the position of the movable lens group based on the moving amount calculated by the moving amount calculation section when the movable lens group is situated on a telescopic side relative to a reference point that is set at a position between the wide-angle end and the telescopic end.

12. An endoscope apparatus comprising:
an imaging optical system that includes a plurality of lens groups each having at least one lens, wherein a single lens group from among the plurality of lens groups is a movable lens group, and wherein the imaging optical system is configured so that an in-focus object distance is changed along with a change in angle of view;
an image sensor;
a plurality of phase sensors;
an acquisition section that acquires phase information from the plurality of phase sensors;
a lens control section that controls a position of the movable lens group; and
a moving amount calculation section that calculates a moving amount of the movable lens group necessary for implementing an in-focus state of an object image of an object formed on the image sensor due to light beams that have passed through the imaging optical system, based on a phase difference that is based on the phase information acquired by the acquisition section, wherein:
the imaging optical system is an optical system that is configured so that the angle of view and the in-focus object distance monotonously decrease as the movable lens group moves from a wide-angle end to a telescopic end,
the moving amount calculation section changes at least one parameter for calculating the moving amount of the movable lens group based on the position of the movable lens group, and calculates the moving amount of the movable lens group based on the at least one parameter having been changed and the phase information, the at least one parameter being selected from among parameters including (i) distance information about a distance from the image sensor to a pupil position, (ii) center-of-gravity distance information about divided pupils, and (iii) ratio information about a ratio of the moving amount to a distance from the image sensor to an image position, and
the lens control section controls the position of the movable lens group based on the moving amount calculated by the moving amount calculation section.

13. A method for controlling an imaging device comprising an imaging optical system, the imaging optical system including a plurality of lens groups each having at least one lens, a single lens group from among the plurality of lens groups being a movable lens group having at least one lens, the imaging optical system being configured so that an in-focus object distance is changed along with a change in angle of view, and the method comprising:
acquiring phase information from a plurality of phase sensors;
calculating a moving amount of the movable lens group necessary for implementing an in-focus state of an object image of an object formed on an image sensor due to light beams that have passed through the imaging optical system, based on a phase difference based on the acquired phase information;
changing at least one parameter for calculating the moving amount of the movable lens group based on the position of the movable lens group, and calculating the moving amount of the movable lens group based on the at least one parameter having been changed and the phase information, the at least one parameter being selected from among parameters including (i) distance information about a distance from the image sensor to a pupil position, (ii) center-of-gravity distance information about divided pupils, and (iii) ratio information about a ratio of the moving amount to a distance from the image sensor to an image position; and
controlling a position of the movable lens group based on the calculated moving amount,
wherein:
the imaging optical system is an optical system that is configured so that the angle of view and the in-focus object distance monotonously decrease as the movable lens group moves from a wide-angle end to a telescopic end, and
the in-focus object distance is a distance from the imaging optical system to the object when the object image is in the in-focus state.

* * * * *